(12) United States Patent
Su

(10) Patent No.: US 10,168,263 B2
(45) Date of Patent: Jan. 1, 2019

(54) HANDHELD CONSTANT-STIFFNESS RING SHEAR APPARATUS AND METHOD FOR USING SAME

(71) Applicant: SHENZHEN UNIVERSITY, Shenzhen, Guangdong Province (CN)

(72) Inventor: Dong Su, Shenzhen (CN)

(73) Assignee: SHENZHEN UNIVERSITY (CN)

( * ) Notice: Subject to any disclaimer, the term of this patent is extended or adjusted under 35 U.S.C. 154(b) by 0 days.

(21) Appl. No.: 15/529,815

(22) PCT Filed: Mar. 30, 2016

(86) PCT No.: PCT/CN2016/077925
§ 371 (c)(1),
(2) Date: May 25, 2017

(87) PCT Pub. No.: WO2016/173365
PCT Pub. Date: Nov. 3, 2016

(65) Prior Publication Data
US 2017/0328824 A1    Nov. 16, 2017

(30) Foreign Application Priority Data

Apr. 29, 2015 (CN) .......................... 2015 1 0212883

(51) Int. Cl.
*G01L 1/00* (2006.01)
*G01N 3/24* (2006.01)

(52) U.S. Cl.
CPC . *G01N 3/24* (2013.01); *G01L 1/00* (2013.01)

(58) Field of Classification Search
CPC ..................................... G01N 3/24; G01L 1/00

USPC .......................................................... 73/815
See application file for complete search history.

(56) References Cited

U.S. PATENT DOCUMENTS

| | | | | |
|---|---|---|---|---|
| 1,657,730 A | * | 1/1928 | Voleske | B23D 29/023 30/249 |
| 3,406,567 A | * | 10/1968 | Terry | G01N 3/24 73/84 |
| 5,639,031 A | * | 6/1997 | Wright | A61L 11/00 241/33 |
| 5,712,431 A | * | 1/1998 | Vilendrer | G01N 3/24 73/841 |
| 2002/0170361 A1 | * | 11/2002 | Vilendrer | G01N 3/24 73/849 |

(Continued)

*Primary Examiner* — Max Noori
(74) *Attorney, Agent, or Firm* — PROI Intellectual Property US

(57) ABSTRACT

A handheld constant-stiffness ring shear apparatus has a base and an annular rigid frame arranged on the base in a sleeved mode. An upper cover is buckled to the top of the rigid frame, a pressure transmission plate is fixed to the upper portion of the upper cover, and a rotary shaft is perpendicularly arranged in the center of the base. The rotary shaft penetrates through the pressure transmission plate and is fixed to the pressure transmission plate. A spanner is fixed to the top end of the rotary shaft, and a digital display instrument is embedded in the spanner. The handheld constant-stiffness ring shear apparatus is convenient to carry, easy to operate, economical and practical, and can be used for measuring the volume chance of a soil sample at a field location under the constant-stiffness condition in the shear force resisting and shearing process.

8 Claims, 1 Drawing Sheet

(56) References Cited

U.S. PATENT DOCUMENTS

2013/0112013 A1* 5/2013 Jeong ............... G01N 3/24
73/862.581

* cited by examiner

HANDHELD CONSTANT-STIFFNESS RING SHEAR APPARATUS AND METHOD FOR USING SAME

CROSS REFERENCE TO RELATED APPLICATIONS

The present application is the US national stage of International Patent Application PCT/CN2016/077925 filed on Mar. 30, 2016, which, in turn, claims priority to Chinese Patent Application CN 201510212883.7 filed on Apr. 29, 2015.

BACKGROUND OF THE INVENTION

Technical Field

The invention relates to the field of characteristics of mechanical stress testing of solid materials, in particular to a handheld constant-stiffness ring shear apparatus and a using method thereof.

Description of Related Art

The ring shear apparatus was developed in the 1920s, however development of the ring shear apparatus almost stopped in the several decades following. Study on the ring shear apparatus began again in the 1960s along with the rise of studies on residual strength, and afterwards, various ring shear apparatuses used in indoor laboratories have been researched and developed.

Existing indoor ring shear apparatuses can be of two types, namely single-ring shear apparatuses and double-ring shear apparatuses, according to the structural characteristics. Compared with other soil test methods, the ring shear apparatuses have the two common advantages that during the test process, the area of the shear plane can be kept unchanged and shearing can be conducted under a continuous displacement condition. According to single-ring shear apparatuses, during the test process, a soil sample is placed into a cylindrical sample box, and vertical pressure and torsional shear force are applied to the sample through a pressurization plate on the upper portion. The single-ring shear apparatuses mainly have the advantage that leakage of the soil sample can be avoided during the shear test process. According to the double-ring shear apparatuses, a soil sample is sheared along a preset plane in the middle of the annular shear boxes which are mutually independent in the vertical direction, so that the purposes of lowering distribution non-uniformity of stress and strain along the shearing plane, reducing resistance between the soil sample and shear rings, and eliminating stress concentration of the edges of the shear rings are hopefully realized.

With the improvement of the technical means, the non-drainage state can be achieved in the shear process under various test conditions by a modern indoor ring shear apparatus through a servo control system and a shear ring seam sensor, and implementation and switching of a drainage test condition and a non-drainage test condition can be guaranteed, and meanwhile, test data can be analyzed and processed more conveniently and faster by the application of computer-controlled and high-sensitivity recording equipment. However, since a modern ring shear test system is increasingly complex and precise, the manufacturing cost and using cost of the modern ring shear apparatuses are increasing gradually, and the daily maintenance fee of the apparatuses is becoming increasingly high. In addition, the existing ring shear apparatuses are complex and large in size, can only be used in an indoor laboratory, cannot be used at a field location, and can only output constant pressure.

BRIEF SUMMARY OF THE INVENTION

The invention aims to provide a handheld constant-stiffness ring shear apparatus and a using method thereof, which are used for measuring the volume change of a soil sample at a field location under the constant stiffness condition in the shear force resisting and shearing process. The handheld constant-stiffness ring shear apparatus is convenient to carry, easy to operate, economical and practical, and output pressure can be adjusted.

According to one technical scheme of the invention, a handheld constant-stiffness ring shear apparatus comprises a base and an annular rigid frame arranged on the base in a sleeved mode, an annular upper cover is buckled to the top of the rigid frame, a pressure transmission plate is fixed to the upper portion of the upper cover, a rotary shaft is perpendicularly arranged in the center of the base, the rotary shaft penetrates through the pressure transmission plate and is fixed to the pressure transmission plate through threads, a spanner is fixed to the top end of the rotary shaft, and a digital display instrument is embedded in the spanner; a spring support is fixed to the side wall of the base through threads, spring guide rods are perpendicularly fixed under the spring support, the upper ends of the spring guide rods are sleeved with limiting nuts, the portions, below the limiting nuts, of the spring guide rods are sleeved with springs, and sliding blocks are pressed to the lower ends of the springs and arranged on the pressure transmission plate; a first clamp is connected between the upper ends of the springs and the pressure transmission plate, and a first dial indicator is mounted on the first clamp; a dial indicator support is further fixed to the side wall of the base and connected with the pressure transmission plate through a second clamp, and a second dial indicator is mounted on the second clamp; the overall dimensions of the handheld constant-stiffness ring shear apparatus are 200 mm*120 mm*240 mm. When the handheld constant-stiffness ring shear apparatus is used, a soil sample is placed into the rigid frame firstly, all the components are debugged, and the initial readings of the digital display instrument, the first dial indicator and the second dial indicator are recorded. The spanner is rotated, the reading on the digital display instrument changes accordingly, the rotary shaft drives the pressure transmission plate and the upper cover to rotate, the soil sample is pressed gradually, the upper cover drives the pressure transmission to descend, the springs in the initial compressed state extend downward immediately and stretch the first clamp, and the reading of the first dial indicator changes along with the stretching of the first clamp. The second clamps can also be stretched downwards along with the descending of the pressure transmission plate, and the reading of the second dial indicator changes accordingly. The average shear stress on the soil sample can be worked out according the reading of the digital display instrument and the inner diameter and the outer diameter of the annular soil sample. The average normal stress on the soil sample can be worked out according to the number and stiffness coefficient of the springs, the reading of the first dial indicator and the inner diameter and the outer diameter of the annular soil sample. The height change of the soil sample can be known according to the reading of the second dial indicator, and then the volume change of the soil sample can be worked out according to the inner diameter and the outer diameter of the soil sample.

The handheld constant-stiffness ring shear apparatus in the technical scheme is small in size, low in weight, low in cost and capable of being used at a field location conveniently, and the weight of the apparatus is only 2 kg; the springs are used for applying vertical force, no external pressure source or loading equipment is needed; ring shear tests under different initial pressure conditions can be carried out by setting different initial compression amounts of the springs; constant-stiffness ring shear tests under different stiffness conditions can be carried out by arranging springs with different stiffness degrees.

Furthermore, the rotary shaft is arranged in a bearing in a sleeved mode, the bearing is perpendicularly fixed to the center of the base. The rotary shaft rotates in the bearing and is small in friction force and flexible in rotation.

Furthermore, limiting piles are arranged at the bottom of the rigid frame, limiting grooves are formed on the base, and the limiting piles are located in the limiting grooves, so that the rigid frame is prevented from horizontally sliding on the base.

Furthermore, a handle is arranged on the outer side of the base. The apparatus can be fixed conveniently, and the handle can be rotated conveniently.

Furthermore, round spacers are arranged on the upper portions of the sliding blocks and make contact with the lower ends of the springs; when the pressure transmission plate rotates, the annular sliding blocks on the pressure transmission plate only slide on the surface of the pressure transmission plate without changing the positions, the round spacers are located under the springs all the time, and thus the springs are prevented from bending.

According to another technical scheme of the invention, a using method of the handheld constant-stiffness ring shear apparatus comprises the following steps that:

S1, the rigid frame is taken out, and a soil sample is evenly placed into the rigid frame; after the soil sample is placed into the rigid steel, the surface of the soil sample is scraped flat, the height of the soil sample is made to meet the requirement, and the rigid frame is placed into the base of the apparatus;

S2, the apparatus is covered with the upper cover, the sliding blocks are placed on the pressure transmission plate, and the spacers are placed on the sliding blocks;

S3, the spring support, the spring guide rods, the limiting nuts and the springs are mounted, and it is ensured that the spring spacers connected with the springs are placed on the annular sliding blocks on the pressure transmission plate;

S4, the limiting nuts are adjusted to make the soil sample in a pre-pressed state;

S5, the spring support, the first dial indicator and the first clamp are mounted, and the initial reading of the first dial indicator is recorded; the dial indicator support, the second dial indicator and the second clamp are mounted, and the initial reading of the second dial indicator is recorded.

S6, the handle of the base is held with one hand, the torque is applied with the other hand through the spanner to rotate the rotary shaft, the rotary shaft drives the pressure transmission plate and the upper cover to rotate, and shear stress is generated on the upper surface of the soil sample to shear the soil sample; during the process, the reading of the first dial indicator, the reading of the second dial indicator and the reading of the digital display instrument are recorded.

S7, after the test is ended, the soil sample is removed, and the average shear stress and the average normal stress acting on the soil sample are worked out according to the reading of the first dial indicator, the reading of the second dial indicator and the reading of the digital display instrument.

The handheld constant-stiffness ring shear apparatus in the technical scheme is small in size, low in weight and capable of being used at a field location conveniently; the springs are used for applying vertical force, no external pressure source or loading equipment is needed; ring shear tests under different initial pressure conditions can be carried out by setting different initial compression amounts of the springs; constant-stiffness ring shear tests under different stiffness conditions can be carried out by arranging springs with different stiffness degrees.

Furthermore, in step S7, the inner diameter and the outer diameter of the annular soil sample are preset to be $R_1$ and $R_2$ correspondingly; suppose that the shear stress $\tau$ on the soil sample is evenly distributed, the torque M acting on the soil sample can be known according to the reading of the digital display instrument in the loading process, and according to the static balance condition, the average shear stress on the soil sample meets the following formula:

$$\tau = \frac{3M}{2\pi(R_2^3 - R_1^3)}$$

in the formula, $\tau$ refers to the average shear stress, M refers to the torque acting on the soil sample, $R_1$ refers to the inner diameter of the annular soil sample, $R_2$ refers to the outer diameter of the annular soil sample, and $\pi$ is 3.14.

Furthermore, in step S7, the compression amount x of the springs is obtained through calculation according to the reading of the first dial indicator, and the normal stress F acting on the soil sample meets the following formula:

$$F = n \cdot k \cdot x$$

in the formula, F refers to the normal stress, k refers to the stiffness coefficient of the springs, and n refers to the number of the springs;

the average normal stress $\sigma_n$ on the soil sample is worked out by means of the normal stress F according to the following formula:

$$\sigma_n = \frac{F}{\pi(R_2^2 - R_1^2)}$$

in the formula, $\sigma_n$ refers to the average normal stress, F refers to the normal stress, $R_1$ refers to the inner diameter of the annular soil sample, $R_2$ refers to the outer diameter of the annular soil sample, and $\pi$ is 3.14.

The handheld constant-stiffness ring shear apparatus and the using method thereof have the beneficial effects that the handheld constant-stiffness ring shear apparatus in the technical scheme is small in size, low in weight and capable of being used at a field location conveniently; the springs are used for applying vertical force, no external pressure source or loading equipment is needed; ring shear tests under different initial pressure conditions can be carried out by setting different initial compression amounts of the springs; constant-stiffness ring shear tests under different stiffness conditions can be carried out by arranging springs with different stiffness degrees.

Figure 1:
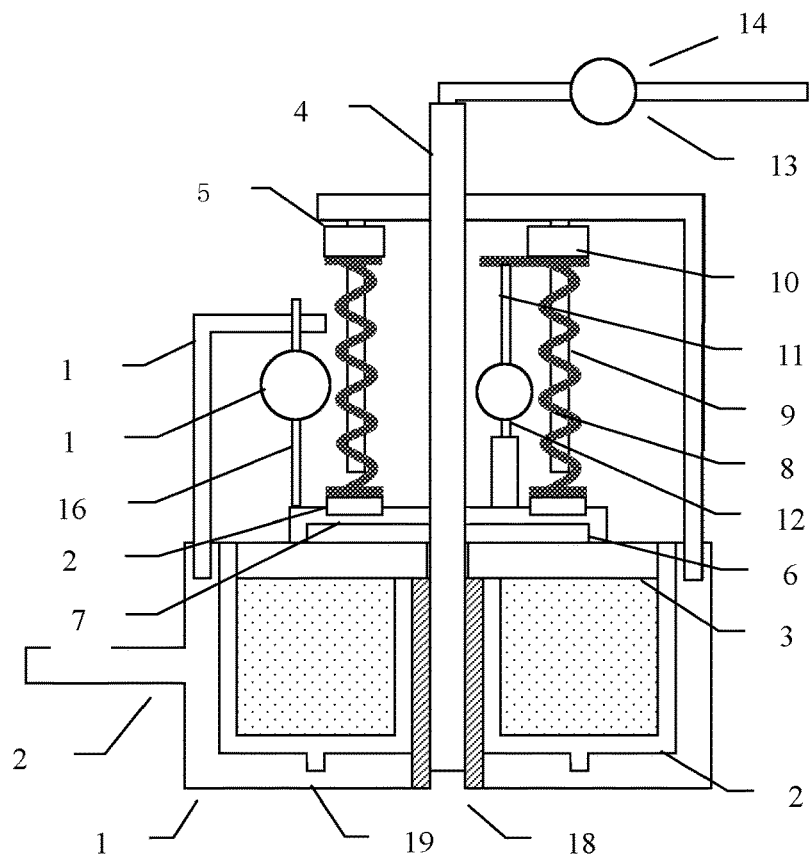
FIG. 1 is a structural schematic diagram of one embodiment of the invention.

Marks in the Drawings: 1—base; 2—rigid frame; 3—upper cover; 4—rotary shaft; 5—spring support; 6—pressure transmission plate; 7—sliding block; 8—spring guide rod; 9—spring; 10—limiting nut; 11—first clamp; 12—first dial indicator; 13—spanner; 14—digital display instrument; 15—dial indicator support; 16—second clamp; 17—second dial indicator; 18—bearing; 19—limiting pile; 20—handle; 21—spacer.

DETAILED DESCRIPTION OF THE INVENTION

Figure 2:
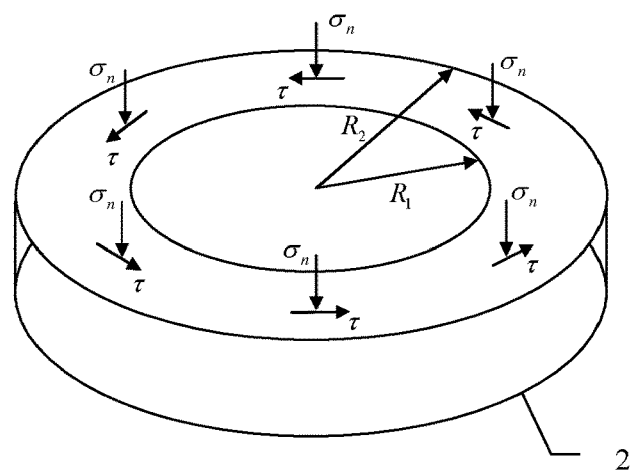
FIG. 2 is a stress distribution diagram of a ring shear sample in another embodiment of the invention.

A further detailed description of preferred embodiments of the invention is given with accompanying drawings as follows:

Please see FIG. 1 and FIG. 2, a handheld constant-stiffness ring shear apparatus comprises a base 1 and an annular rigid frame 2 arranged on the base 1 in a sleeved mode, an annular upper cover 3 is buckled to the top of the rigid frame 2, a pressure transmission plate 6 is fixed to the upper portion of the upper cover 3, a rotary shaft 4 is perpendicularly arranged in the center of the base 1, the rotary shaft 4 penetrates through the pressure transmission plate 6 and is fixed to the pressure transmission plate 6 through threads, a spanner 13 is fixed to the top end of the rotary shaft 4, and a digital display instrument 14 is embedded in the spanner 13; a spring support 5 is fixed to the side wall of the base 1 through threads, spring guide rods 8 are perpendicularly fixed under the spring support 5, the upper ends of the spring guide rods 8 are sleeved with limiting nuts 10, the portions, below the limiting nuts 10, of the spring guide rods 8 are sleeved with springs 9, and sliding blocks 7 are pressed to the lower ends of the springs 9 and arranged on the pressure transmission plate 6; a first clamp 11 is connected between the upper ends of the springs 9 and the pressure transmission plate 6, and a first dial indicator 12 is mounted on the first clamp 11; a dial indicator support 15 is further fixed to the side wall of the base 1 and connected with the pressure transmission plate 6 through a second clamp 16, and a second dial indicator 17 is mounted on the second clamp 16; the overall dimensions of the handheld constant-stiffness ring shear apparatus are 200 mm*120 mm*240 mm. When the handheld constant-stiffness ring shear apparatus is used, a soil sample is placed into the rigid frame 2 firstly, all the components are debugged, and the initial readings of the digital display instrument 14, the first dial indicator 12 and the second dial indicator 17 are recorded. The spanner 13 is rotated, the reading on the digital display instrument 14 changes accordingly, the rotary shaft 4 drives the pressure transmission plate 6 and the upper cover 3 to rotate, the soil sample is pressed gradually, the upper cover 3 drives the pressure transmission 6 to descend, the springs 9 in the initial compressed state extend downward immediately and stretch the first clamp 11, and the reading of the first dial indicator 12 changes along with the stretching of the first clamp 11. The second clamps 16 can also be stretched downwards along with the descending of the pressure transmission plate 6, and the reading of the second dial indicator 17 changes accordingly. The average shear stress of the soil sample can be worked out according the reading of the digital display instrument 14 and the inner diameter and the outer diameter of the annular soil sample. The average normal stress of the soil sample can be worked out according to the number and stiffness coefficient of the springs 9, the reading of the first dial indicator 12 and the inner diameter and the outer diameter of the annular soil sample. The height change of the soil sample can be known according to the reading of the second dial indicator 17, and then the volume change of the soil sample can be worked out according to the inner diameter and the outer diameter of the soil sample.

The handheld constant-stiffness ring shear apparatus in the technical scheme is small in size, low in weight, low in cost and capable of being used at a field location conveniently, and the weight of the apparatus is only 2 kg; the springs 9 are used for applying vertical force, no external pressure source or loading equipment is needed; ring shear tests under different initial pressure conditions can be carried out by setting different initial compression amounts of the springs 9; constant-stiffness ring shear tests under different stiffness conditions can be carried out by arranging springs 9 with different stiffness degrees.

Please see FIG. 1, the rotary shaft 4 is arranged in a bearing 18 in a sleeved mode, the bearing 18 is perpendicularly fixed to the center of the base 1. The rotary shaft 4 rotates in the bearing 18 and is small in friction force and flexible in rotation.

Please see FIG. 1, limiting piles 19 are arranged at the bottom of the rigid frame 2, limiting grooves are formed on the base 1, and the limiting piles 19 are located in the limiting grooves, so that the rigid frame 2 is prevented from horizontally sliding on the base 1.

Please see FIG. 1, a handle 20 is arranged on the outer side of the base 1. The apparatus can be fixed conveniently, and the handle 20 can be rotated conveniently.

Please see FIG. 1, round spacers 21 are arranged on the upper portions of the sliding blocks 7 and make contact with the lower ends of the springs 9; when the pressure transmission plate 6 rotates, the annular sliding blocks 7 on the pressure transmission plate 6 only slide on the surface of the pressure transmission plate 6 without changing the positions, the round spacers 21 are located under the springs 9 all the time, and thus the springs 9 are prevented from bending.

Please see FIG. 1, a using method of the handheld constant-stiffness ring shear apparatus comprises the following steps that:

S1, the rigid frame is taken out, and a soil sample is evenly placed into the rigid frame; after the soil sample is placed into the rigid steel, the surface of the soil sample is scraped flat, the height of the soil sample is made to meet the requirement, and the rigid frame is placed into the base 1 of the apparatus;

S2, the apparatus is covered with the upper cover 3, the sliding blocks 7 are placed on the pressure transmission plate 6, and the spacers 21 are placed on the sliding blocks 7;

S3, the spring support 5, the spring guide rods 8, the limiting nuts 10 and the springs 9 are mounted, and it is ensured that the spring spacers 21 connected with the springs 9 are placed on the annular sliding blocks 7 on the pressure transmission plate 6;

S4, the limiting nuts 10 are adjusted to make the soil sample in a pre-pressed state;

S5, the spring support 5, the first dial indicator 12 and the first clamp 11 are mounted, and the initial reading of the first dial indicator 12 is recorded; the dial indicator support 15, the second dial indicator 17 and the second clamp 16 are mounted, and the initial reading of the second dial indicator 17 is recorded.

S6, the handle 20 of the base 1 is held with one hand, the torque is applied with the other hand through the spanner 13 to rotate the rotary shaft 4, the rotary shaft 4 drives the pressure transmission plate 6 and the upper cover 3 to rotate, and shear stress is generated on the upper surface of the soil sample to shear the soil sample; in the process, the reading of the first dial indicator 12, the reading of the second dial indicator 17 and the reading of the digital display instrument 14 are recorded.

S7, after the test is ended, the soil sample is removed, and the average shear stress and the average normal stress acting on the soil sample are worked out according to the reading of the first dial indicator 12, the reading of the second dial indicator 17 and the reading of the digital display instrument 14.

In step S7, the inner diameter and the outer diameter of the annular soil sample are preset to be $R_1$ and $R_2$ correspondingly; suppose that the shear stress $\tau$ on the soil sample is evenly distributed, the torque M acting on the soil sample can be known according to the reading of the digital display instrument 14 in the loading process, and according to the static balance condition, the average shear stress on the soil sample meets the following formula:

$$\tau = \frac{3M}{2\pi(R_2^3 - R_1^3)} \quad (1)$$

in the formula, $\tau$ refers to the average shear stress, M refers to the torque acting on the soil sample, $R_1$ refers to the inner diameter of the annular soil sample, $R_2$ refers to the outer diameter of the annular soil sample, and $\pi$ is 3.14.

The following five sets of data are provided for the formula (1):

| Group | $R_1$ (mm) | $R_2$ (mm) | M (N · m) | $\tau$ (kPa) |
|---|---|---|---|---|
| 1 | 50 | 90 | 12.65 | 10 |
| 2 | | | 25.30 | 20 |
| 3 | | | 37.95 | 30 |
| 4 | | | 50.60 | 40 |
| 5 | | | 63.25 | 50 |

In step S7, the compression amount x of the springs 9 is obtained through calculation according to the reading of the first dial indicator 12, and the normal stress F acting on the soil sample meets the following formula:

$$F = n \cdot k \cdot x \quad (2)$$

in the formula, F refers to the normal stress, k refers to the stiffness coefficient of the springs 9, and n refers to the number of the springs 9;

The following five sets of data are provided for the formula (2):

| Group | n | k (N/mm) | x (mm) | F (N) |
|---|---|---|---|---|
| 1 | 4 | 50 | 1.76 | 351.86 |
| 2 | 4 | 50 | 3.52 | 703.72 |
| 3 | 4 | 50 | 5.28 | 1055.58 |
| 4 | 4 | 50 | 7.04 | 1407.43 |
| 5 | 4 | 50 | 8.80 | 1759.29 |

The average normal stress $\sigma_n$ on the soil sample is worked out by means of the normal stress F according to the following formula:

$$\sigma_n = \frac{F}{\pi(R_2^2 - R_1^2)} \quad (3)$$

in the formula, $\sigma_n$ refers to the average normal stress, F refers to the normal stress, $R_1$ refers to the inner diameter of the annular soil sample, $R_2$ refers to the outer diameter of the annular soil sample, and $\pi$ is 3.14.

The following five sets of data are provided for the formula (3):

| Group | $R_1$ (mm) | $R_2$ (mm) | F (N) | $\sigma_n$ (kPa) |
|---|---|---|---|---|
| 1 | 50 | 90 | 351.86 | 20 |
| 2 | | | 703.72 | 40 |
| 3 | | | 1055.58 | 60 |
| 4 | | | 1407.43 | 80 |
| 5 | | | 1759.29 | 100 |

The handheld constant-stiffness ring shear apparatus in the embodiment is small in size, low in weight and capable of being used at a field location conveniently; the springs 9 are used for applying vertical force, no external pressure source or loading equipment is needed; ring shear tests under different initial pressure conditions can be carried out by setting different initial compression amounts of the springs 9; constant-stiffness ring shear tests under different stiffness conditions can be carried out by arranging springs 9 with different stiffness degrees.

The forgoing content is a further detailed description of the invention with the preferred embodiments, but specific embodiments of the invention are not limited to the description. For those skilled in the technical field of the invention, several simple deductions or replacements can be made without deviating from the concept of the invention, and the simple deductions or replacements are all included in the protection scope of the invention.

What is claimed is:

1. A handheld constant-stiffness ring shear apparatus, comprising a base and an annular rigid frame arranged on the base in a sleeved mode, characterized in that an annular upper cover is buckled to the top of the rigid frame, a pressure transmission plate is fixed to the upper portion of the upper cover, a rotary shaft is perpendicularly arranged in the center of the base, the rotary shaft penetrates through the pressure transmission plate and is fixed to the pressure transmission plate, a spanner is fixed to the top end of the rotary shaft, and a digital display instrument is embedded in the spanner; a spring support is fixed to the side wall of the base, spring guide rods are perpendicularly fixed under the spring support, the upper ends of the spring guide rods are sleeved with limiting nuts, the portions, below the limiting nuts, of the spring guide rods are sleeved with springs, and sliding blocks are pressed to the lower ends of the springs and arranged on the pressure transmission plate; a first clamp is connected between the upper ends of the springs and the pressure transmission plate, and a first dial indicator is mounted on the first clamp; a dial indicator support is further fixed to the side wall of the base and connected with the pressure transmission plate through a second clamp, and a second dial indicator is mounted on the second clamp; the overall dimensions of the handheld constant-stiffness ring shear apparatus are 200 mm*120* mm*240 mm.

2. The handheld constant-stiffness ring shear apparatus according to claim 1, characterized in that the rotary shaft is arranged in a bearing in a sleeved mode, and the bearing is perpendicularly fixed to the center of the base.

3. The handheld constant-stiffness ring shear apparatus according to claim 2, characterized in that limiting piles are arranged at the bottom of the rigid frame, limiting grooves are formed on the base, and the limiting piles are located in the limiting grooves.

4. The handheld constant-stiffness ring shear apparatus according to claim 3, characterized in that a handle is arranged on the outer side of the base.

5. The handheld constant-stiffness ring shear apparatus according to claim 4, characterized in that round spacers are arranged on the upper portions of the sliding blocks and make contact with the lower ends of the springs.

6. A using method of the handheld constant-stiffness ring shear apparatus according to claim 5, characterized by comprising the following steps that:
   S1, the rigid frame is taken out, and a soil sample is evenly placed into the rigid frame;
   after the soil sample is placed into the rigid steel, the surface of the soil sample is scraped flat, the height of the soil sample is made to meet the requirement, and the rigid frame is placed into the base of the apparatus;
   S2, the apparatus is covered with the upper cover, the sliding blocks are placed on the pressure transmission plate, and the spacers are placed on the sliding blocks;
   S3, the spring support, the spring guide rods, the limiting nuts and the springs are mounted, and it is ensured that the spring spacers connected with the springs are placed on the annular sliding blocks on the pressure transmission plate;
   S4, the limiting nuts are adjusted to place the soil sample in a pre-pressed state;
   S5, the spring support, the first dial indicator and the first clamp are mounted, and the initial reading of the first dial indicator is recorded; the dial indicator support, the second dial indicator and the second clamp are mounted, and the initial reading of the second dial indicator is recorded;
   S6, the handle of the base is held with one hand, a torque is applied with the other hand through the spanner to rotate the rotary shaft, the rotary shaft drives the pressure transmission plate and the upper cover to rotate, and shear stress is generated on the upper surface of the soil sample to shear the soil sample; during the process, the reading of the first dial indicator, the reading of the second dial indicator and the reading of the digital display instrument are recorded;
   S7, after the test is ended, the soil sample is removed, and the average shear stress and the average normal stress acting on the soil sample are worked out according to the reading of the first dial indicator, the reading of the second dial indicator and the reading of the digital display instrument.

7. The using method of the handheld constant-stiffness ring shear apparatus according to claim 6, characterized in that in step S7, the inner diameter and the outer diameter of the annular soil sample are preset to be $R_1$ and $R_2$ correspondingly; suppose that the shear stress τ on the soil sample is evenly distributed, the torque M acting on the soil sample can be known according to the reading of the digital display instrument in the loading process, and according to the static balance condition, the average shear stress on the soil sample meets the following formula:

$$\tau = \frac{3M}{2\pi(R_2^3 - R_1^3)}$$

in the formula, τ refers to the average shear stress, M refers to the torque acting on the soil sample, $R_1$ refers to the inner diameter of the annular soil sample, $R_2$ refers to the outer diameter of the annular soil sample, and π is 3.14.

8. The using method of the handheld constant-stiffness ring shear apparatus according to claim 6, characterized in that in step S7, the compression amount x of the springs is obtained through calculation according to the reading of the first dial indicator, and the normal stress F acting on the soil sample meets the following formula:

$$F = n \cdot k \cdot x$$

in the formula, F refers to the normal stress, k refers to the stiffness coefficient of the springs, and n refers to the number of the springs;

the average normal stress $\sigma_n$ on the soil sample is worked out by means of the normal stress F according to the following formula:

$$\sigma_n = \frac{F}{\pi(R_2^2 - R_1^2)}$$

in the formula, $\sigma_n$ refers to the average normal stress, F refers to the normal stress, $R_1$ refers to the inner diameter of the annular soil sample, $R_2$ refers to the outer diameter of the annular soil sample, and π is 3.14.

* * * * *